(12) United States Patent
Evans

(10) Patent No.: US 7,584,675 B2
(45) Date of Patent: Sep. 8, 2009

(54) CONNECTOR ENABLING MULTIPLE SAMPLING OF SEALED ENVIRONMENT

(75) Inventor: Roy L. Evans, Indianapolis, IN (US)

(73) Assignee: Enzon Pharmaceuticals, Bridgewater, NJ (US)

( * ) Notice: Subject to any disclaimer, the term of this patent is extended or adjusted under 35 U.S.C. 154(b) by 140 days.

(21) Appl. No.: 11/780,292

(22) Filed: Jul. 19, 2007

(65) Prior Publication Data
US 2009/0019954 A1    Jan. 22, 2009

(51) Int. Cl.
*G01N 1/20* (2006.01)
(52) U.S. Cl. .................................. 73/863.41; 73/865.6
(58) Field of Classification Search .............. 73/863.41, 73/863.45, 863.56, 863.81–863.83, 863.85, 73/863.86, 865.6; 137/262, 333, 561 A, 137/597, 602, 627, 630.16, 637.3, 883
See application file for complete search history.

(56) References Cited

U.S. PATENT DOCUMENTS

| | | | | |
|---|---|---|---|---|
| 4,549,567 A | * | 10/1985 | Horton | 137/262 |
| 5,601,115 A | * | 2/1997 | Broerman | 137/595 |
| 6,142,178 A | * | 11/2000 | Whiteside | 137/561 A |
| 6,374,860 B2 | * | 4/2002 | Xu et al. | 137/884 |
| 7,293,475 B2 | * | 11/2007 | Furey et al. | 73/863.31 |
| 2001/0003290 A1 | * | 6/2001 | Xu et al. | 137/885 |
| 2006/0272432 A1 | * | 12/2006 | Belongia | 73/864.63 |

* cited by examiner

*Primary Examiner*—John Fitzgerald
(74) *Attorney, Agent, or Firm*—Lucas & Mercanti, LLP

(57) ABSTRACT

Connector which provide conduits between a sealed environment and an exterior of the environment includes a housing, a plurality of internal conduits extending from a first side of the housing, each adapted to communicate with a respective sampling device situated in the sealed environment, and a single external conduit extending from a second side of the housing opposite the first side and adapted to communicate with a measurement device exterior of the sealed environment. The housing is constructed to enable each internal conduits to alternatingly align with the external conduit such that each sampling device is able to communicate with the measurement device. By providing a connector which is able to provide a flow passage between multiple sampling devices and a single measurement device, at different times, it is not necessary to enter the sealed environment in order to configure a single sampling device in communication with the measurement device.

22 Claims, 4 Drawing Sheets

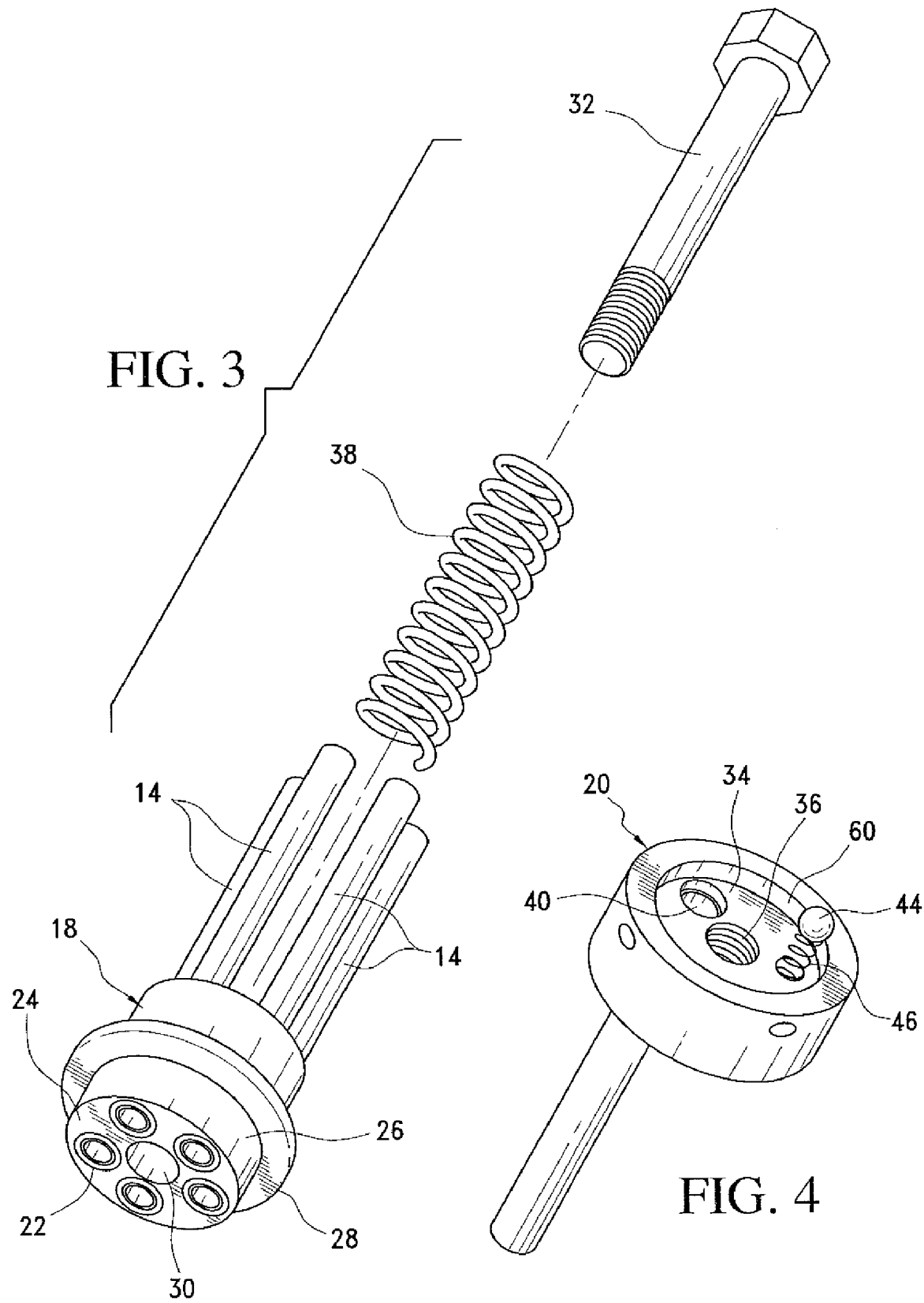

CONNECTOR ENABLING MULTIPLE SAMPLING OF SEALED ENVIRONMENT

FIELD OF THE INVENTION

The present invention relates generally to connectors which provide conduits between a sealed environment and an exterior of the environment, and more particularly to connectors which provide conduits between a plurality of sampling devices situated in a sealed environment and a measurement device situated exterior of the environment which allows the measurement device to be selectively coupled to each sampling device.

BACKGROUND OF THE INVENTION

During pharmaceutical testing, materials are typically situated in a sealed environment defined by a testing device during the testing process. One device which enables creation of a sealed environment for pharmaceutical testing is a half suit isolator. During typical use of such an isolator, an access door or hatch to the isolator is opened, the materials for conducting the test are inserted into the interior of the isolator, the hatch is then closed and the testing process is started.

At specified times, it is necessary to conduct measurements to obtain data about the sealed environment for the purposes of, e.g., satisfying HEPA certification requirements. For example, it is often necessary to measure particles in the sealed environment at various stages during the testing process, e.g., after the completion of each of a series of tests being conducted during the testing process. To this end, a sampling device or probe, such as an isokinetic probe, is placed in the interior of the isolator and connected to a measurement device such as a particle counter.

In a conventional measurement process, after the measurement device completes the measurement and obtains data from the probe, which usually occurs during or after completion of a test in the series of tests personnel enter the half suit isolator, the probe was then repositioned and the air was allowed to settle down, and the next test performed followed by another measurement. This procedure was repeated until appropriate measurements were obtained at each probe location and after the completion of each test. As a result, the measurement phase became a rather lengthy, time-consuming and labor-intensive process.

It is therefore desirable to reduce the amount of time and labor required to obtain measurements from a plurality of probes situated at various locations in a sealed environment.

OBJECTS AND SUMMARY OF THE INVENTION

It is an object of the present invention to provide a connector which provides conduits between a sealed environment and an exterior of the environment.

It is another object of the present invention to provide a connector which provides conduits between a plurality of sampling devices situated in an interior of a sealed environment and a measurement device situated exterior of the environment which allows the measurement device to be selectively coupled to each sampling device.

It is another object of the present invention to provide a method for sampling a sealed environment.

It is yet another object of the present invention to provide an arrangement for testing conditions in a sealed environment defined in a testing apparatus.

In order to achieve at least one of these objects, one embodiment of a connector for connecting a plurality of sampling devices to a measurement device in accordance with the invention includes a housing, a plurality of internal conduits extending from a first side of the housing, each adapted to communicate with a respective sampling device, and a single external conduit extending from a second side of the housing opposite the first side and adapted to communicate with the measurement device. The housing is constructed to enable each internal conduit to alternatingly align with the external conduit such that each sampling device is able to communicate with the measurement device, at a different time. To this end, the housing is provided with an adjustable mechanism for alternatingly aligning each internal conduit with the external conduit. By providing a connector which is able to provide a flow passage between multiple sampling devices and a single measurement device, at different times, when the sampling devices are situated in a sealed environment, it is not necessary to repeatedly enter the half suit isolator in order to reposition a sampling device when sampling at different locations in the sealed environment is required.

The housing may include a first part to which the internal conduits are mounted and a second part to which the external conduit is mounted, the first and second parts being rotatable relative to one another to provide for the alternating alignment of one of the internal conduits relative to the external conduit. An adjustable mechanism can be provided for alternatingly aligning each internal conduit with the external conduit, e.g., by enabling rotation of the second housing part relative to the first housing part. This mechanism may be designed to alternatingly align an opening of the second housing part leading to the external conduit with each opening of the first housing part leading to an internal conduit.

A positioning device is optionally provided in the housing for aiding alignment of each opening in the first housing part with the opening of the second housing part, e.g., a ball and spring device which is designed to enter into one of the internal conduits when another internal conduit is aligned with the external conduit. The positioning device ideally provides a detectable effect, such as an audible or manually detectable response, when an internal conduit aligns with the external conduit.

In one embodiment, a connecting mechanism is provided to connect the first housing part to the second housing part and may bias the first housing part against the second housing part. This ensures a tight seal through the junction between the external conduit and the internal conduits.

An arrangement for testing conditions in a sealed environment defined in a testing apparatus in accordance with the invention includes a plurality of sampling devices arranged in the sealed environment, a measurement device arranged exterior to the sealed environment to provide data about the sealed environment, a connector for connecting the sampling devices to the measurement device which may be as described above and is adapted to be arranged in a frame of the testing apparatus, a first connecting mechanism for connecting each internal conduit to a respective sampling device and a second connecting mechanism for connecting the external conduit to the measurement device. Since the housing enables each internal conduit to alternatingly align with the external conduit, each sampling device is able to communicate with the measurement device to allow the measurement device to perform a measurement via the sampling device. The sampling devices may be isokinetic probes and the measurement device may be a particle counter. The testing apparatus may be a half suit isolator or a vialwash tunnel. The connecting mechanisms may be tubes or may be connectors adapted to provide a direct connection between the sampling devices or measurement device and the conduit.

A method for testing conditions in a sealed environment defined in a testing apparatus in accordance with the invention includes arranging a plurality of sampling devices in the sealed environment, arranging a measurement device exterior to the sealed environment to provide data about the sealed environment, arranging a single connector in a frame of the testing apparatus, the connector being as described above, connecting each internal conduit to a respective sampling device, connecting the external conduit to the measurement device, sealing the environment, and adjusting the housing to alternatingly align each internal conduit with the external conduit and conducting a measurement via the measurement device when each internal conduit is aligned with the external conduit without opening the sealed environment. Adjustment of the housing may entail rotating the second housing part relative to the first housing part. The test apparatus may be a half suit isolator or a vialwash tunnel. The sampling devices may be isokinetic probes and the measurement device may a particle counter.

BRIEF DESCRIPTION OF THE DRAWINGS

The following drawings are illustrative of embodiments of the invention and are not meant to limit the scope of the invention as encompassed by the claims.

FIG. 3 is a perspective view of a first housing part of the connector shown in FIG. 1.

FIG. 4 is a perspective view of a second housing part of the connector shown in FIG. 1.

DETAILED DESCRIPTION OF THE INVENTION

Figure 1:
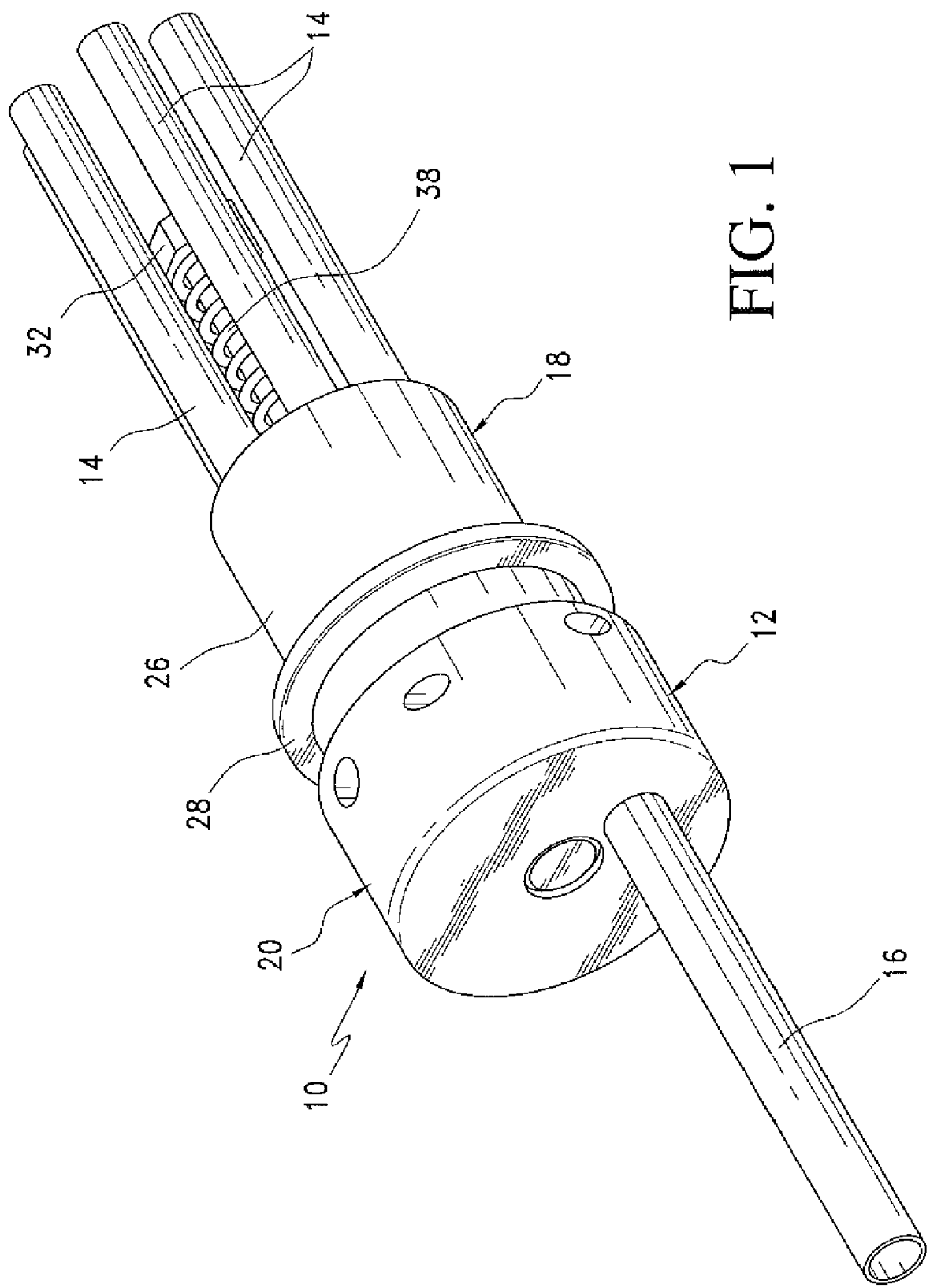
FIG. 1 is a perspective view of a first embodiment of a connector in accordance with the invention.
Figure 2:
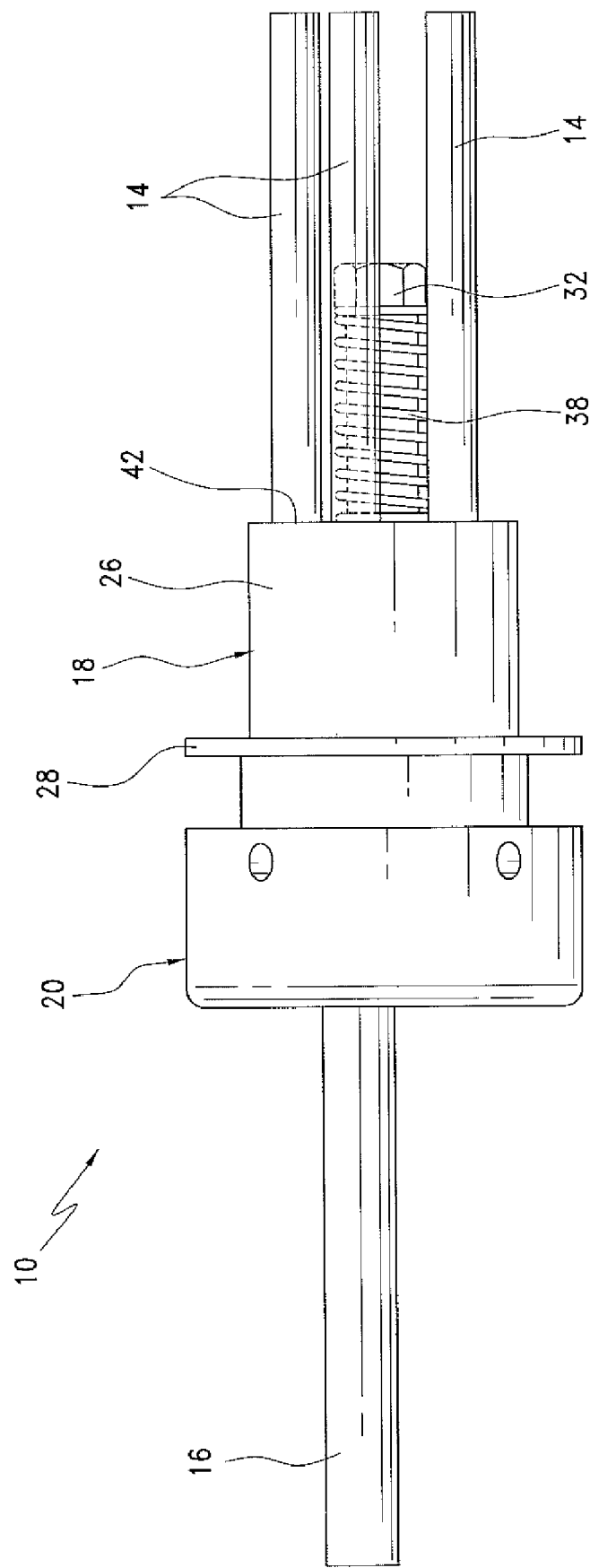
FIG. 2 is a side view of the connector shown in FIG. 1.

Referring to the accompanying drawings wherein like reference numerals refer to the same or similar elements, FIGS. 1 and 2 show a connector in accordance with the invention designated generally as 10. Connector 10 includes a housing 12, a plurality of internal conduits 14 extending from one side of the housing 12 and a single external conduit 16 extending from the other side of the housing 12. Internal conduits 14 are arranged to be situated in an interior of a sealed environment while external conduit 16 is arranged to be situated exterior of the sealed environment. Nevertheless, the terms internal and external should not be considered to limit the application of the connector 10 and are provided simply for ease of explanation of the invention.

Housing 12 includes a first housing part 18 and a second housing part 20 rotatable relative to one another. Thus, if the first housing part 18 is fixed, e.g., to the frame of the testing apparatus defining the sealed environment, then the second housing part 20 would be rotatable relative to the first housing part 18. Rotation of the second housing part 20 may be achieved manually by grasping the second housing part 20.

Conduits 14 are mounted to or otherwise arranged in connection with the first housing part 18 and the conduit 16 is mounted to or otherwise arranged in connection with the second housing part 20. For example, conduits 14 may be partially embedded in the first housing part 18 while conduit 16 may be partially embedded in the second housing part 20.

Conduits 14 each have a substantially cylindrical form, at least at a free end portion extending beyond the edge of the first housing part 18, to enable a tube to be arranged around them. When used in a half suit isolator, the tubes would connect to sampling devices or probes, such as isokinetic probes, positioned at different locations in the sealed environment defined by the isolator. As shown, there are five conduits 14 arranged in a circle about a central region of the housing 12. However, other numbers, arrangements, shapes and types of conduits are envisioned for connectors in accordance with the invention. At a minimum, a free end region of the conduits 14 should be adapted for connection to a tube which in turn may be connected to a sampling device or alternatively, the conduits 14 may each be adapted for direct connection to a sampling device.

Each conduit 14 extends through, and is fixed to, a substantially cylindrical body 26 of the first housing part 18. Conduits 14 lead to or define openings 22 in an inner surface 24 of the first housing part 18 (see FIG. 3). A flange 28 extends around the cylindrical body 26 and defines a space between it and the second housing part 20 which has a larger diameter than the diameter of the cylindrical body 26 (see FIG. 2). Appropriate sealing mechanisms may be provided around the openings 22 to prevent leakage of samples passing through conduits 14, such as rubber O-rings.

The form of cylindrical body 26 and flange 28 are designed to enable the connector 10 to be use with a Tri-Clover type clamping system when mounted onto the apparatus defining the sealed environment, e.g., a half suit isolator or Vialwash tunnel. Thus, for use, a port in the frame of the apparatus would be opened, the connector 10 would be placed into the port and clamped by the Tri-Clover type clamping system to seal the connector 10 against the frame of the apparatus. However, the shape and form of the body 26 may be alternatively designed for use with any apparatus which defines a sealed environment and has one or more ports through which instruments and/or tubes extend during use of the apparatus and an associated clamping system for the instruments and/or tubes to maintain the integrity of the sealed environment.

Cylindrical body 26 includes a channel 30, shown in FIG. 3, through which a bolt 32 passes to engage with the second housing part 20. To this end, the forward end of bolt 32 may be threaded with a corresponding thread 36 formed on an inner surface 34 of the second housing part 20 (see FIG. 4). A compression spring 38 is arranged around bolt 32 to aid in maintaining a tight seal between the first and second housing parts 18, 20. An annular surface 42 is formed by the first housing part 18, from which the conduits 14 extend and which provides a seat for the compression spring 38. Compression spring 38 also allows for slight play between the first and second housing parts 18, 20 to enable the second housing part 20 to be rotated relative to the first housing part 18 when the first housing part 18 is fixed in position.

As shown in FIG. 4, the inner surface 34 of the second housing part 20 includes a single opening 40 which communicates with the conduit 16. Conduit 16 has a substantially cylindrical form, at least at a free end portion extending beyond the edge of the second housing part 20, to enable a tube to be arranged around it. Such a tube would connect at its opposite end to a measurement device (shown in FIG. 5), such as a commercially available particle counter. At a minimum, a free end region of the conduit 16 should be adapted for connection to a tube which in turn may be connected to a measurement device or alternatively, conduit 16 may be adapted for direct connection to a measurement device.

The second housing part 20 may include a positioning device for aiding alignment of each of opening 22 in the inner surface 24 of the first housing part 18 with the opening 40 in the inner surface 34 of the second housing part 20. In the illustrated embodiment, this positioning device is embodied as a ball 44 and spring 46 connected at one end to the ball 44 and at an opposite end to the inner surface 34 of the second housing part 20 (see FIG. 4). This ball and spring device provides a sensory indication, e.g., by sound or touch, when one of the conduits 14 aligns with conduit 16. That is, an audible "click" may be heard when the ball 44 is urged by the spring 46 into one of the conduits 14, with another conduit 14 then being in alignment with conduit 16. To this end, the ball 44 and spring 46 must be appropriately positioned relative to the opening 40. However, the ball and spring device does not impede rotation of the second housing part 20 relative to the first housing part 18 but rather when the second housing part 20 is manually rotated, the ball 44 is urged rearward against the bias of the spring 46 to move along the inner surface 24 of the first housing part 18 until it is pressed into the next opening 22.

The second housing part 20 includes a rim 60 around the inner surface 34 which has an internal dimension larger than the outer dimension of the inner housing part 18 around inner surface 24 thereof. In this manner, as the inner housing part 18 is pressed against the outer housing part 20, a tight seal is formed to prevent samples or particles flowing through the connector 10 from being released.

To further aid in alignment of each conduit 14 with the conduit 16, external indicia may be provided on the first and/or second housing parts 18, 20. This indicia may be a single line on the second housing part 20 corresponding to the circumferential position of the conduit 16 and a plurality of lines on the first housing part 18, each corresponding to the circumferential location of a respective conduit 14. Alternatively, the indicia may be a single line on the first housing part 18, possibly but not necessarily corresponding to the circumferential position of one of the conduits 14, and a plurality of lines on the second housing part 20, each arranged so that when it aligns with the single line on the first housing part 18, one of the conduits 14 is in alignment with conduit 16.

The dimensions of the conduits 14, 16 may vary depending on the connector mechanism from the conduits 14, 16 to the sampling devices or measurement device. For example, the diameter of the conduits 14, 16 may be ¼ inch or ⁵⁄₁₆ inch. A larger diameter conduit would be particularly useful for use with current, high velocity particle counters. The dimensions of the ball 44 and spring 46 are also variable as necessary to provide the desired positioning effect. The dimensions of the bolt 32 and compression spring 38 are also variable as necessary to achieve the effect of allowing rotation of the second housing 20 relative to the first housing part 18 while maintaining a seal at the junction between the conduit 16 and the conduit 14 aligned therewith. The bolt 32 may be a ¼×20 threaded bolt or a ⅜×16 threaded bolt. Instead of screwing the bolt 32 into the second housing part 20 from the side on which the conduits 14 are located, it is possible to construct the connector 10 so that the bolt and compression spring pass through the second housing part into the first housing part in order to adjustably connect the first and second housing parts together.

Figure 5:
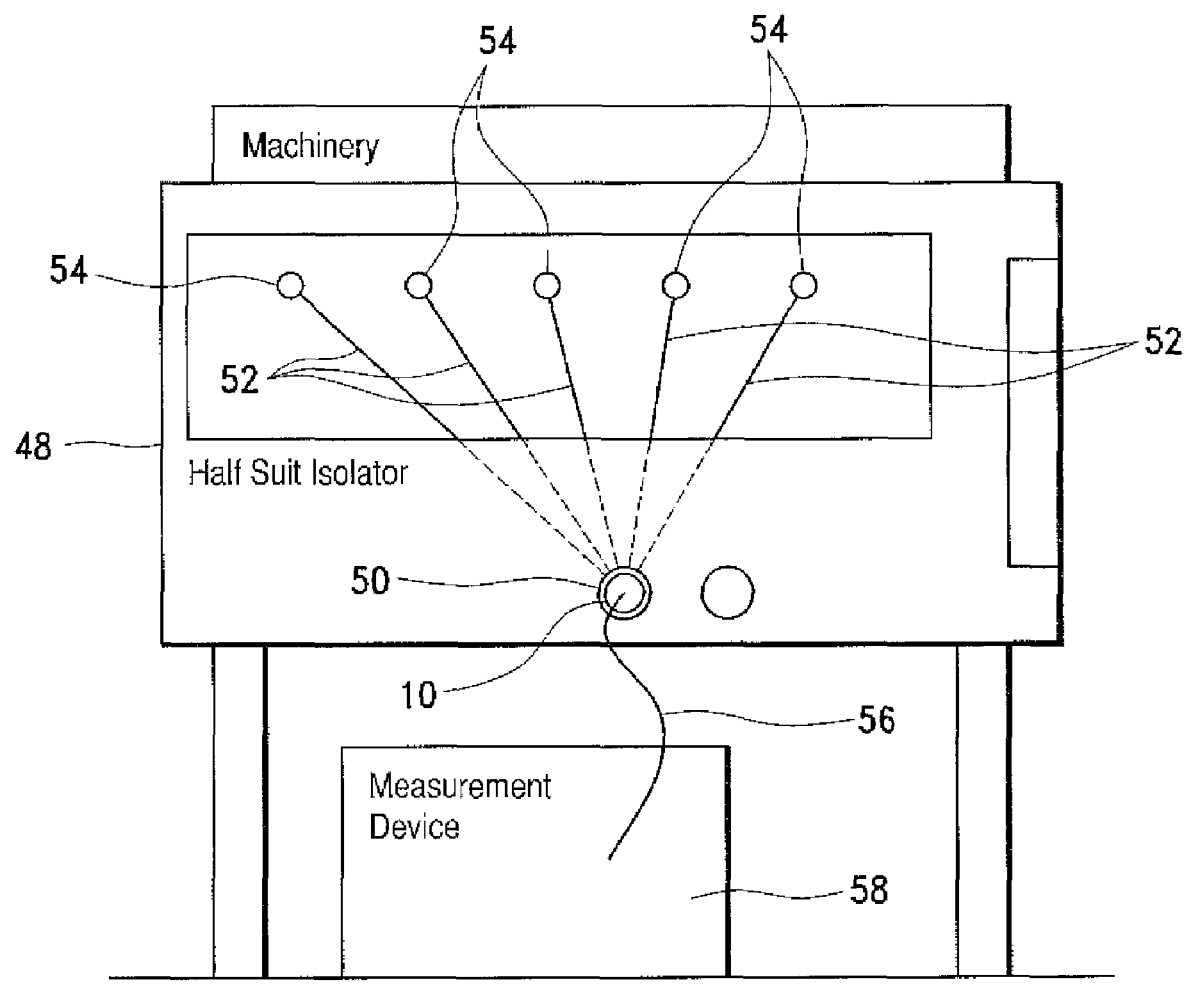
FIG. 5 is a schematic of a device in connection with which the connector shown in FIG. 1 is used.

Referring now to FIG. 5, in an exemplifying use of the connector 10 in accordance with the invention, the connector 10 is installed into connection with the apparatus defining the sealed environment, such as a half suit isolator 48, with the five conduits 14 situated in the sealed environment and the single conduit 16 exterior of the sealed environment. Specifically, the connector 10 is installed into a port 50 formed on the isolator 48 and clamped therein by a conventional clamping mechanism in a manner known to those skilled in the art. When the connector 10 is not present, the port may be provided with a protective cover as known to those skilled in the art.

A tube 52 is attached at one end to each of the conduits 14 and the other end of each tube 52 is attached to an isokinetic probe 54. The probes 54 are situated at desired locations in the sealed environment, e.g., at different locations or locations required by the certification procedure. Appropriate mounting devices are provided to mount the probes 54 in the sealed environment, e.g., to the walls or base of the isolator 48. Another tube 56 is attached at one end to the conduit 16 and at its opposite end to a measurement device 58 such as a particle counter. Attachment or engagement of the tubes 52, 56 to the conduits 14, 16 may be achieved by any technique known to those skilled in the art.

Once the tubes 52, 56 are all attached to conduits 14, 16, the testing process is then started. Using a conventional half suit isolator 48, the tunnel fans would be started.

In an initial state of the connector 10, preferably one of the conduits 14 is aligned with the conduit 16. It is also possible that none of the conduits 14 initially align with the conduit 16 in which case, the second housing part 20 is rotated relative to the first housing part 18 to bring one of the conduits 14 into alignment with conduit 16. Once one of the conduits 14 is in alignment with conduit 16, the measurement device 58 is operated to perform, for example, a count of specific particles in the sealed environment. This may entail drawing air into the measurement device 58 from the probe 54 in the sealed environment.

When the particle count is finished, the second housing part 20 is rotated relative to the first housing part 18 to bring a different conduit 14 into alignment with conduit 16. The measurement device 58 is then operated to perform another particle count. Rotation of the second housing part 20 relative to the first housing part 18 continues until all of the conduits 14 have been aligned with the conduit 16 and particle counts from all of the different probe locations have been performed.

Using the invention, it is therefore possible to perform multiple measurements, such as particle counts, without disturbing the air in the sealed environment. Since entering the half suit isolator each time to move the isokinetic probe takes time, the invention significantly reduces the amount of time required to perform multiple measurements and therefore greatly simplifies testing procedures, such as HEPA certification procedures. Moreover, the probes can be readily positioned at different locations in the sealed environment to enable sampling from multiple locations in the sealed environment.

The connector illustrated in the drawings is designed to be compatible for testing apparatus which use a Tri-Clover type clamping system to enable instruments and/or tubes to be inserted through one or more ports in its frame into the sealed, interior environment. This compatibility is provided mainly as a result of the structure of the housing 12. The housing 12 could be easily modified to be compatible for apparatus which use other clamping systems, such as national pipe thread, and thereby enable use or a connector in accordance with the invention with virtually any type of machinery which requires multiple stations or locations to be checked, e.g., via sampling devices, without requiring relocation of a single sampling device.

Although the connector is described above for use with a measurement device and isokinetic probes which enable air to be drawn through the probes into the measurement device, the connector can generally be used to allow alternating passage of any type of fluids, whether liquids or gases, between a single device external to a sealed environment and a plurality of devices in the interior of the sealed environment. The fluids could either flow from the plurality of internally-situated devices to the single externally-situated device or vice versa.

Another embodiment of a connector in accordance with the invention includes a disc adapted to be sealingly mounted to the frame or housing of the testing apparatus defining the sealed environment, a plurality of internal conduits extending to one side of the disc and a similar number of external conduits extending to the opposite side of the disc. The internal and external conduits are connected to or formed integral with the disc. The free end of each internal conduit, when positioned in the sealed environment, can be connected to a probe, e.g., an isokinetic probe, via a tube. Each external conduit is in communication with or possibly even in alignment with a respective one of the internal conduits, possibly with the external conduits formed as extensions of the internal conduits or vice versa.

In this embodiment, tubes connected to the external conduits can be connected to different measurement devices, or to a coupling member which alternately connects each tube to the same measurement device. For use in a similar manner as the exemplifying use of connector 10 described above, rotation of the disc would not be not required since there is a passageway from each probe in the sealed environment to a measurement device, namely, through a tube extending between the probe and an internal conduit, through the communicating external conduit, and through a tube extending between the external conduit and the measurement device.

Although manual rotation of the second housing part 20 relative to the first housing part 18 is described above to selectively align one of the conduits 14 with the conduit 16, it is conceivable that the second housing part 20 can be designed to enable use of a tool, such as a wrench, which is inserted into one or more corresponding cavities formed in the second housing part 20 and then rotated to cause rotation of the second housing part 20 relative to the first housing part 18. Other rotation techniques, whether manual or automatic, can also be applied in accordance with the invention.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

The invention claimed is:

1. A connector for connecting a plurality of sampling devices to a measurement device, comprising:
    a housing;
    a plurality of internal conduits extending from a first side of said housing, each of said internal conduits being adapted to communicate with a respective one of the sampling devices; and
    a single external conduit extending from a second side of said housing opposite said first side, said single external conduit being adapted to communicate with the measurement device,
    said housing being arranged to enable each of said internal conduits to alternatingly align with said external conduit such that each of the sampling devices is able to communicate with the measurement device.

2. The connector of claim 1, further comprising an adjustment mechanism for alternatingly aligning each of said internal conduits with said external conduit.

3. The connector of claim 1, wherein said housing comprises a first part to which said internal conduits are mounted and a second part to which said external conduit is mounted, said first and second housing parts being rotatable relative to one another.

4. The connector of claim 3, further comprising connecting means for connecting said first housing part and said second housing part together.

5. The connector of claim 4, wherein said connecting means are biased to press said one of first and second housing parts against the other of said first and second housing parts.

6. The connector of claim 3, further comprising an adjustment mechanism for alternatingly aligning each of said internal conduits with said external conduit by rotating said second housing part relative to said first housing part.

7. The connector of claim 6, wherein said first housing part has the same number of openings as the number of said internal conduits with each leading to a respective one of said internal conduits and said second part has a single opening leading to said external conduit, said mechanism being arranged to alternatingly align said opening of said second housing part with each of said openings of said first housing part.

8. The connector of claim 7, further comprising a positioning device for aiding alignment of each of said openings in said first housing part with said opening of said second housing part.

9. An arrangement for testing conditions in a sealed environment defined in a testing apparatus, comprising:
    a plurality of sampling devices arranged in the sealed environment;
    a measurement device arranged exterior to the sealed environment to provide data about the sealed environment;
    a connector for connecting said sampling devices to said measurement device, said connector being adapted to be arranged in a frame of the testing apparatus and comprising a housing, a plurality of internal conduits extending from a first side of said housing, and a single external conduit extending from a second side of said housing opposite said first side;
    first connecting means for connecting each of said internal conduits to a respective one of said sampling devices; and
    second connecting means for connecting said external conduit to said measurement device,
    said housing being arranged to enable each of said internal conduits to alternatingly align with said external conduit such that each of said sampling devices is able to communicate with said measurement device.

10. The arrangement of claim 9, wherein said sampling devices are isokinetic probes and said measurement device is a particle counter.

11. The arrangement of claim 9, wherein said first connecting means comprise a plurality of internal tubes and said second connecting means comprise an external tube.

12. The arrangement of claim 9, further comprising an adjustment mechanism for alternatingly aligning each of said internal conduits with said external conduit.

13. The arrangement of claim 9, wherein said housing comprises a first part to which said internal conduits are mounted and a second part to which said external conduit is mounted, said first and second housing parts being rotatable relative to one another.

14. The arrangement of claim 13, further comprising connecting means for connecting said first housing part and said second housing part together.

15. The arrangement of claim 14, wherein said connecting means are biased to press one of said first and second housing parts against the other of said first and second housing parts.

16. The arrangement of claim 13, further comprising an adjustment mechanism for alternatingly aligning each of said internal conduits with said external conduit by rotating said second housing part relative to said first housing part.

17. The arrangement of claim 16, wherein said first housing part has the same number of openings as the number of said internal conduits with each leading to a respective one of said internal conduits and said second part has a single opening leading to said external conduit, said mechanism being arranged to alternatingly align said opening of said second housing part with each of said openings of said first housing part.

18. The arrangement of claim 17, further comprising a positioning device for aiding alignment of each of said openings in said first housing part with said opening of said second housing part.

19. A method for testing conditions in a sealed environment defined in a testing apparatus, comprising:
arranging a plurality of sampling devices prior to sealing the environment;
arranging a measurement device exterior to the sealed environment;
arranging a single connector in a frame of the testing apparatus, the connector including a housing, a plurality of internal conduits extending from a first side of the housing, and a single external conduit extending from a second side of the housing opposite the first side, the housing being arranged to enable each of the internal conduits to alternatingly align with the external conduit;
connecting each of the internal conduits to a respective one of the sampling devices prior to sealing the environment;
connecting the external conduit to the measurement device;
sealing the environment; and then
adjusting the housing to alternatingly align each of the internal conduits with the external conduit and conducting a measurement via the measurement device when each internal conduit is aligned with the external conduit without opening the sealed environment.

20. The method of claim 19, wherein the housing comprises a first part to which the internal conduits are mounted and a second part to which the external conduit is mounted, the step of adjusting the housing comprising rotating the second housing part relative to the first housing part.

21. The method of claim 19, further comprising arranging a positioning device in the housing to aid alignment of each of the internal conduits with the external conduit.

22. The method of claim 19, wherein the sampling devices are isokinetic probes and the measurement device is a particle counter.

\* \* \* \* \*